US006274706B1

(12) United States Patent
Emorine et al.

(10) Patent No.: US 6,274,706 B1
(45) Date of Patent: *Aug. 14, 2001

(54) INTRON/EXON OF THE HUMAN AND MOUSE BETA 3-ADRENERGIC RECEPTOR GENES

(75) Inventors: Laurent Emorine; Stefano Marullo; Donny Strosberg, all of Paris (FR)

(73) Assignee: Centre National de la Recherche Scientifique, Paris (*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/450,962

(22) Filed: May 25, 1995

Related U.S. Application Data

(60) Division of application No. 08/117,829, filed on Sep. 8, 1993, now abandoned, which is a continuation-in-part of application No. 07/721,571, filed on Sep. 3, 1991, now Pat. No. 5,288,607.

(30) Foreign Application Priority Data

Jan. 25, 1989 (FR) .................................................. 8900918

(51) Int. Cl.$^7$ ................................................. C07K 14/705
(52) U.S. Cl. .......................................................... 530/350
(58) Field of Search .......................... 530/350; 536/22.1, 536/23.1, 29.5, 24.3, 24.31

(56) References Cited

U.S. PATENT DOCUMENTS

| 5,364,772 | * | 11/1994 | Granneman et al. | ................ | 435/69.1 |
| 5,610,282 | * | 3/1997 | Sibley et al. | .................. | 530/395 |

FOREIGN PATENT DOCUMENTS

| 9008775 | 8/1990 | (WO) . |
| 9212246 | 7/1992 | (WO) . |
| WO 94/02590 | 2/1994 | (WO) . |

OTHER PUBLICATIONS

Arch et al. "Atypical β–adrenoreceptor on brown . . . " Nature vol. 309 pp. 163–165 (1984).
Emorine et al. "Structure of the gene for human β$_2$–a–drenergic . . . " PNAS vol. 84 p. 6995–6999 (1987).

Yarden et al. "Avian β–adrenergic receptor: Primary Structure . . . " PNAS vol. 83, p. 6795–6799 (1986).

Lerner, Richard "Tapping The immunological repertoire . . . " Nature vol. 299 p. 592–596 (Oct. 14, 1982).

Bahouth et al. "Subclassification of β–Adreng. Recept . . . " Molecular Pharmacology 34:318–326 1988.

Spronsen et al., "The promoter and intron/exon structure of the human and mouse beta3–adrenergic–receptor genes," European Journal of Biochemistry, vol. 213, No. 3, pp. 1117–1124, May 1993.*

Lelias et al., "Molecular cloning of a human beta3–adrenergic receptor cDNA," FEBS Letters, vol. 324, No. 2, pp. 127–130, Jun. 14, 1993.*

Nahmias et al. Molecular characterization of the mouse 3–adrenergic receptor: relationship with the atypical receptor of adipocytes. EMBO Journal. Vol. 10, No. 12, pp. 3721–3727, Dec. 1991.*

Kaplan et al., "Biologie Moléculaire et Médecine," 1989, pp. 487–490.

Nahmias et al., "Molecular characterization of the mouse β3–adrenergic receptor: relationship with the atypical receptor of adipocytes," 1991, vol. 10, No. 12, pp. 3721–3727.

Bahouth et al., "Subclassification of β–Adrenergic of Rat Fat Cells: A Re–Evaluation," Sep. 8, 1987, pp. 318–326.

Frielle et al., "Proc. Natl. Acad. Sci. USA 84 (1987)".

Emorine et al., "Molecular Characterization of the Human β$_3$ –Adrenergic Receptor," Sep. 8, 1989, Vol. 245, pp. 1118–1121.

Féve et al., "Atypical β–Adrenergic Receptor in 3T3–F442A Adipocytes," Oct. 25, 1991, vol. 266, No. 30, 20329–20336.

* cited by examiner

Primary Examiner—John Ulm
(74) Attorney, Agent, or Firm—Hunton & Williams

(57) ABSTRACT

The present invention relates to the intron and exon structure of the gene encoding β3 adrenergic receptor polypeptides of mouse and human origin, which polypeptides are useful in a procedure for studying the effects of various chemical agents on the β3 adrenergic receptor coupled to adenylate cyclase and hormone-sensitive lipases.

1 Claim, 7 Drawing Sheets

```
agggtcgggaagcatgcgatgtgtccgtggtcaactttttgagtgtggagtttattaagagaaggtggatggctttgcttggagagaaaagggaacgaggagtagcgaaccaaaatgg  1994
gacccagggtccttttcttcgcctgctggtcgtcggctttaggggtagaagcaaagagggcgagcgggccgtcgtttcgtctctgtgtccacgcgggaatgcagtgtgcatctcagctcactgcagtct  2114
gaggactctcgcctgctggtcaagcgatcctcccacctgagcctccagctgcttggactagcgagcccaccaatccagctatttttaaaattctgtgaagtgggggtctt  2234
tgaactcctggctgcttctttgaacttctgtctccgagttctctgcctcagtgatcctctgcctcaaagcattacaggcgagccaggcgccgggtcggctcgtcctagttttggttt  2354
gctatgtgtcccaggcttgtgccccccccgattctgccatcactagacctggctcgacttgaaggcaggcagtgccccccaagcctcgcctcggctctcagttctggg  2474
tccagctcagttctttgacacgtgtgaggtgagaatccacttcgggtatgaagtaacagttgtgagtgagcgtccaggttccaggtctttcgctcactgttgctccttcac  2594
ttttctcaaaggttttgacagctgtgtgggctgggctggctgggtgtgccctggcgttttgtgtaactaaatatgcttgcacactgggctccttcacttgctccttcac  2714
taggatgggggtgggctgggtggctgggtgggctgggtgcctggaaggacaagaacaactctgtgatcagaaactgtg  2945
ccaggtctattatctccacttttttcccag  G  GCT  TCT  TGG  GGA  GTT  TCT  tag  gcctgaaggacaagaacaactctgtgatcagaaactctgg  408
                                  A   S   W   G   V   S   *
Acceptor
ccccctgtttcagaatgagtccatggattcccgctgtgacactctacctccagaacctgacgactgggccatgtgacccaagaggatcctaccaagtggttttcaccatcctc  3065
ttgctctctgtctgagagatgttttctaaaccccagcttgaacttcactcctcctcccagtgtagtgtccagttggcctgctcaggtgcccaggcggagtag  3185
gcttgcctgtgcagtcagtgagtgctgagtgcttagggcaagaagctccctggttccttatatctctggttccttattactgctcaagcagtgcctctcacttagcctaagtcagagtagaga  3305
ttcagaaggactttggggttttgggagctccaggttcataagaaggtgaacattagaacagatcccctttctttcctttgcaatcagatatatcatccactactgaatgcagttcat  3545
gcagcagggtagaaagaccaagatttggggtttatctctggttccttattactgctcaagcagtgcctctcacttagcctacctcacacagtg  3425
cctcggcccccttccctcgttgtttctttcataatccacttactcccctttctctgctgctttgacagaggcgtaaattaggcctaatcctactctttttcctta  3665
                                                                                            aataa
atgttcatcaaagaaaa  3683
```

AMINO-ACID SEQUENCE OF THE HUMAN B3-ADRENERGIC RECEPTOR GENE

```
            10         20         30         40         50         60         70         80
     MAPWPHENSS LAPWPDLPTL APNTANTSGL PGVPWEAALA GALLALAVLA TVGGNLLVIV AIAWTPRLQT MTNVFVTSLA
            90        100        110        120        130        140        150        160
     AADLVMGLLV VPPAATLALT GHWPLGATGC ELWTSVDVLC VTASIETLCA LAVDRYLAVT NPLRYGALVT KRCARTAVVL
           170        180        190        200        210        220        230        240
     VWVVSAAVSF APIMSQWWRV GADAEAQRCH SNPRCCAFAS NMPYVLLSSS VSFYLPLLVM LFVYARVFVV ATRQLRLLRG
           250        260        270        280        290        300        310        320
     ELGRFPPEES PPAPSRSLAP APVGTCAPPE GVPACGRRPA RLLPLREHRA LCTLGLIMGT FTLCWLPFFL ANVLRALGGP
           330        340        350        360        370        380        390        400
     SLVPGPAFLA LNWLGYANSA FNPLIYCRSP DFRSAFRRLL CRCGRRLPPE PCAAARPALF PSGVPAARSS PAQPRLCQRL

DGASWGVS
```

FIG. 4

AMINO-ACID SEQUENCE OF THE MOUSE B3-ADRENERGIC RECEPTOR GENE

```
            10         20         30         40         50         60         70         80
     MAPWPHRNGS LALWSDAPTL DPSAANTSGL PGVPWAAALA GALLALATVG GNLLVIIAIA RTPRLQTITN VFVTSLAAAD
            90        100        110        120        130        140        150        160
     LVVGLLVMPP GATLALTGHW PLGETGCELW TSVDVLCVTA SIETLCALAV DRYLAVTNPL RYGTLVTKRR ARAAVVLVWI
           170        180        190        200        210        220        230        240
     VSAAVSFAPI MSQWWRVGAD AEAQECHSNP RCCSFASNMP YALLSSSVSF YLPLLVMLFV YARVFVVAKR QRHLLRRELG
           250        260        270        280        290        300        310        320
     RFSPEESPPS PSRSPSPATG GTPAAPDGVP PCGRRPARLL PLREHRALRT LGLIMGIFSL CWLPFFLANV LRALAGPSLV
           330        340        350        360        370        380        390        400
     PSGVFIALNW LGYANSAFNP VIYCRSPDFR DAFRRLLCSY GGRGPEEPRA VTFPASPVEA RQSPPLNRFD GYEGARPFPT
```

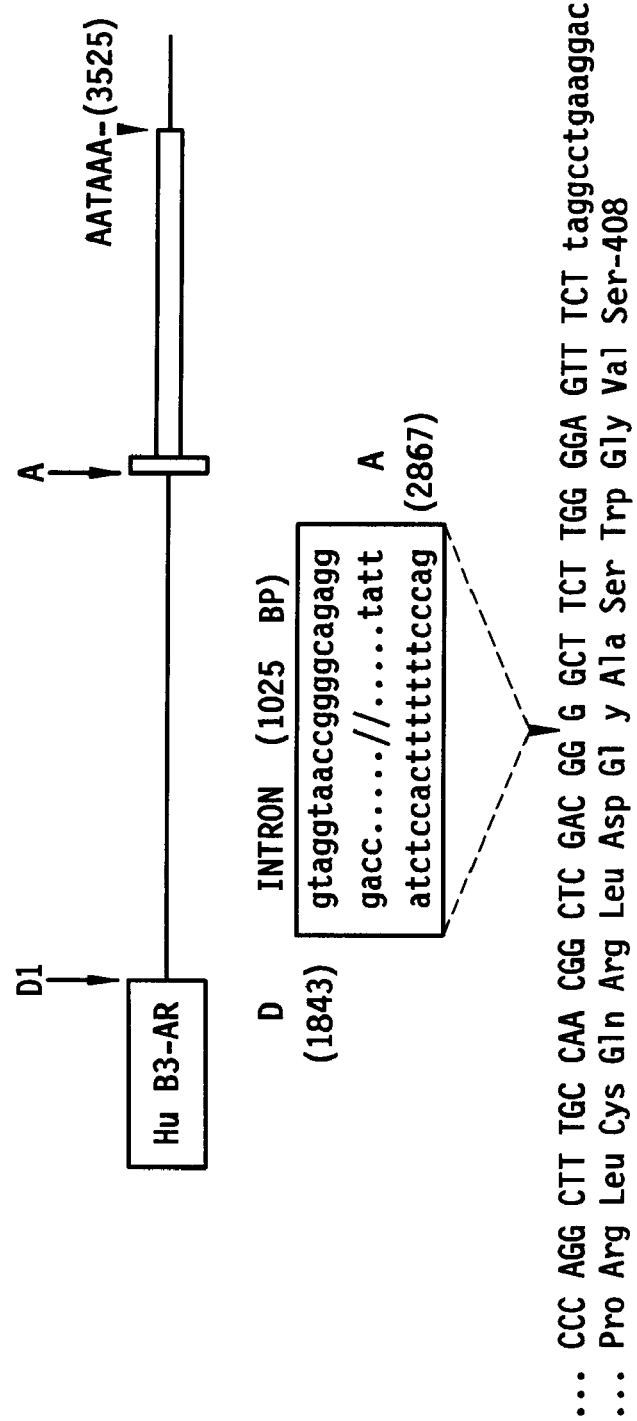

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 3683 bases
      (B) TYPE: nucleic acid
      (C) STRANDEDNESS: single
      (D) TOPOLOGY: linear (xi) SEQUENCE DESCRIPTION: SEQ ID NO: 1:

```
AGATCTCACC AAGCTGAGGT CTTGGGAGAG GAGATACTGG CTGAGCCCTA          50

TTACTTAATT TAAAATACCT TAGGGGAGGC CACCCAAGTG GATGCGGGGC         100

TCCTGTGAAT CCTTTGCTTG ACTCCAGCGG GTTACCTTTG CCTCTGATAC         150

ATAAAGGGTG GGGATGGGAG CGCTCTCCTC TCTCCTTCCC CTGCCTTGCT         200

GTGGGAACTT CTGGGAAAGG AGGTGCAGGG CTCCAGGAAG CCAGTGCCCA         250

GGGAGTGCTA TGCTGAGTCC AGGAGCCTGG CCACGGCAGG GGTGGACAGA         300

TGGTGGCAGA GGAACCACGG TGTCCCTTCC TCCAGATTTA GCTAAAGGAA         350

ACGTGGAGCA TCCCATTGGC CATCCTCCCC ACTCTCCAAT TCGGCTCCAG         400

AGGCCCCTCC AGACTATAGG CAGCTGCCCC TTTAAGCGTC GCTACTCCTC         450

CCCCAAGAGC GGTGGCACCG AGGGAGTTGG GGTGGGGGGA GGCTGAGCGC         500

TCTGGCTGGG ACAGCTAGAG AAGATGGCCC AGGCTGGGGA AGTCGCTCTC         550

ATGCCTTGCT GTCCCCTCCC CTGAGCCAGG TGATTTGGGA GACCCCCTCC         600

TTCCTTCTTT CCCTACCGCC CCACGCGCGA CCCGGGGATG GCTCCGTGGC         650

CTCACGAGAA CAGCTCTCTT GCCCCATGGC CGGACCTCCC CACCCTGGCG         700

CCCAATACCG CCAACACCAG TGGGCTGCCA GGGGTTCCGT GGGAGGCGGC         750

CCTAGCCGGG GCCCTGCTGG CGCTGGCGGT GCTGGCCACC GTGGGAGGCA         800

ACCTGCTGGT CATCGTGGCC ATCGCCTGGA CTCCGAGACT CCAGACCATG         850

ACCAACGTGT TCGTGACTTC GCTGGCCGCA GCCGACCTGG TGATGGGACT         900

CCTGGTGGTG CCGCCGGCGG CCACCTTGGC GCTGACTGGC CACTGGCCGT         950

TGGGCGCCAC TGGCTGCGAG CTGTGGACCT CGGTGGACGT GCTGTGTGTG        1000

ACCGCCAGCA TCGAAACCCT GTGCGCCCTG GCCGTGGACC GCTACCTGGC        1050

TGTGACCAAC CCGCTGCGTT ACGGCGCACT GGTCACCAAG CGCTGCGCCC        1100
```

| | |
|---|---|
| GGACAGCTGT GGTCCTGGTG TGGGTCGTGT CGGCCGCGGT GTCGTTTGCG | 1150 |
| CCCATCATGA GCCAGTGGTG GCGCGTAGGG GCCGACGCCG AGGCGCAGCG | 1200 |
| CTGCCACTCC AACCCGCGCT GCTGTGCCTT CGCCTCCAAC ATGCCCTACG | 1250 |
| TGCTGCTGTC CTCCTCCGTC TCCTTCTACC TTCCTCTTCT CGTGATGCTC | 1300 |
| TTCGTCTACG CGCGGGTTTT CGTGGTGGCT ACGCGCCAGC TGCGCTTGCT | 1350 |
| GCGCGGGGAG CTGGGCCGCT TTCCGCCCGA GGAGTCTCCG CCGGCGCCGT | 1400 |
| CGCGCTCTCT GGCCCCGGCC CCGGTGGGGA CGTGCGCTCC GCCCGAAGGG | 1450 |
| GTGCCCGCCT GCGGCCGGCG GCCCGCGCGC CTCCTGCCTC TCCGGGAACA | 1500 |
| CCGGGCCCTG TGCACCTTGG GTCTCATCAT GGGCACCTTC ACTCTCTGCT | 1550 |
| GGTTGCCCTT CTTTCTGGCC AACGTGCTGC GCGCCCTGGG GGGCCCCTCT | 1600 |
| CTAGTCCCGG GCCCGGCTTT CCTTGCCCTG AACTGGCTAG GTTATGCCAA | 1650 |
| TTCTGCCTTC AACCCGCTCA TCTACTGCCG CAGCCCGGAC TTTCGCAGCG | 1700 |
| CCTTCCGCCG TCTTCTGTGC CGCTGCGGCC GTCGCCTGCC TCCGGAGCCC | 1750 |
| TGCGCCGCCG CCCGCCCGGC CCTCTTCCCC TCGGGCGTTC CTGCGGCCCG | 1800 |
| GAGCAGCCCA GCGCAGCCCA GGCTTTGCCA ACGGCTCGAC GGGTAGGTAA | 1850 |
| CCGGGGCAGA GGGACCGGCG GCTCAGGGTC GGGAAGCATG CGATGTGTCC | 1900 |
| GTGGGTCAAC TTTTTGAGTG TGGAGTTTAT TAAGAGAAGG TGGGATGGCT | 1950 |
| TTGCTTGGAG AGAAAAGGGA ACGAGGAGTA GCGAACCAAA ATGGGACCCA | 2000 |
| GGGTCCTTTT CTTTCCGGAT CCAGTCACTA GGGTAGAAGC AAAGGAGGGC | 2050 |
| GAGCGGGCCG TCGTTCCTCA CCCAAGGACC CAAGGTGCGC CACCGGAAAG | 2100 |
| CGCTGCGGTG TCCCGAGGAC TCTCGCCTCG CCTGGTCGGC TTTAGGGATT | 2150 |
| TTTTTTTTTT TTAAATAGAG ACAGGGTTTC GTCTCTGTCG CCCACGCGGG | 2200 |
| AATGCAGTGG TGCGATCTCA GCTCACTGCA GTCTTGAACT CCTGGCTCCT | 2250 |
| GGGCTCAAGC GATCCTCCCA CCTCAGCCTC CTGAGTATCT GGGACTACAG | 2300 |
| GCGAGCCCCA CCAATCCCAG CTATTTTTAA AATTTCTTGT AGAGATGGGG | 2350 |
| TCTTGCTATG TTGCCCAGGC TTGTCTTGAA CTTCTGGCCT CAAGTGATCC | 2400 |
| TTCTGCCTCA GCCTTCCAAA GCATTAGGAT TACAGGCCGG AGCCAGGGCG | 2450 |
| CCGGGTCGGC TCTAGTTTTG GTTTTCCAGC TCAGTTCTTT GCCCCCCTCC | 2500 |
| CCCGATTTCT TGCCATCACT AGACCTGGCT CGGACTTGAA GGCAGGGCTA | 2550 |
| GTGCCCCCCC ACCCGCCCCC CAAGCCCTCG GCCTCAGTTC TGGGTTTTCT | 2600 |
| CAAAGGTTTG ACAGCTGTGG AGGTGAGAAT CCACTTCCGG TATGAAGTAC | 2650 |
| AGTTGTGAGT GAGGAGCCTG TGAGTGCAGA TGTGTGCCCC CCGCTCCCT | 2700 |
| GGGCTGGGTT GGAGTAGGGA TGGGGTGGGG CGTGTGTGGC TGGGTGGTGC | 2750 |
| CCTGGCGTTT TTGTGTAACT AAATATGCGT TCCAGGGTCT CTGATCTCTG | 2800 |
| TCATTCCCCT CAGTGCACCT GTTGCTCCTT TCACCCCAGG GTCTATTATC | 2850 |
| TCCACTTTTT TTCCCAGGGC TTCTTGGGGA GTTTCTTAGG CCTGAAGGAC | 2900 |
| AAGAAGCAAC AACTCTGTTG ATCAGAACCT GTGGAAAACC TCTGGCCTCT | 2950 |
| GTTCAGAATG AGTCCCATGG GATTCCCCGG CTGTGACACT CTACCCTCCA | 3000 |
| GAACCTGACG ACTGGGCCAT GTGACCCAAG GAGGGATCCT TACCAAGTGG | 3050 |

-continued

```
GTTTTCACCA TCCTCTTGCT CTCTGTCTGA GAGATGTTTT CTAAACCCCA         3100

GCCTTGAACT TCACTCCTCC CTCAGTGGTA GTGTCCAGGT GCCGTGGAGC         3150

AGCAGGCTGG CTTTGGTAGG GGCACCCATC ACCCGGCTTG CCTGTGCAGT         3200

CAGTGAGTGC TTAGGGCAAA GAGAGCTCCC CTGGTTCCAT TCCTTCTGCC         3250

ACCCAAACCC TGATGAGACC TTAGTGTTCT CCAGGCTCTG TGGCCCAGGC         3300

TGAGAGCAGC AGGGTAGAAA AGACCAAGAT TTGGGGTTTT ATCTCTGGTT         3350

CCCTTATTAC TGCTCTCAAG CAGTGGCCTC TCTCACTTTA GCCATGGAAT         3400

GGCTCCGATC TACCTCACAG CAGTGTCAGA AGGACTTCGC CAGGGTTTTG         3450

GGAGCTCCAG GGTTCATAAG AAGGTGAACC ATTAGAACAG ATCCCTTCTT         3500

TTCCTTTTGC AATCAGATAA ATAAATATCA CTGAATGCAG TTCATCCTCG         3550

GCCCCCTTTC CCTCCGTTTG TTTTCTTTTC ATAATCCACT TACTCCCTTC         3600

CCTTCTACTC TGCTGGCTTT TGACAGAGGC GTAAATTAGG CCTAATCCTC         3650

ACTCTTTTCT TCCTAATGTT CATCAAAGAA AAA                          3683
```

(2) INFORMATION FOR SEQ ID NO: 2:

(i) SEQUENCE CHARACTERISTICS:
        (A) LENGTH: 408 residues
        (B) TYPE: amino acid
        (D) TOPOLOGY: linear (ii) MOLECULE TYPE:
        (A) DESCRIPTION: polypeptide (xi) SEQUENCE DESCRIPTION: SEQ ID NO: 2:

```
Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
            20                  25                  30

Val Pro Trp Glu Ala Ala Leu Ala Gly Ala Leu Leu Ala Leu Ala Val
        35                  40                  45

Leu Ala Thr Val Gly Gly Asn Leu Leu Val Ile Val Ala Ile Ala Trp
    50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
            100                 105                 110

Trp Thr Ser Val Asp Val Leu Cys Val Thr Ala Ser Ile Glu Thr Leu
        115                 120                 125

Cys Ala Leu Ala Val Asp Arg Tyr Leu Ala Val Thr Asn Pro Leu Arg
    130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
        195                 200                 205

Ser Ser Val Ser Phe Tyr Leu Pro Leu Leu Val Met Leu Phe Val Tyr
```

```
                    210                 215                 220
Ala Arg Val Phe Val Val Ala Thr Arg Gln Leu Arg Leu Leu Arg Gly
225                 230                 235                 240

Glu Leu Gly Arg Phe Pro Pro Glu Glu Ser Pro Pro Ala Pro Ser Arg
                    245                 250                 255

Ser Leu Ala Pro Ala Pro Val Gly Thr Cys Ala Pro Pro Glu Gly Val
                    260                 265                 270

Pro Ala Cys Gly Arg Arg Pro Ala Arg Leu Leu Pro Leu Arg Glu His
                    275                 280                 285

Arg Ala Leu Cys Thr Leu Gly Leu Ile Met Gly Thr Phe Thr Leu Cys
                    290                 295                 300

Trp Leu Pro Phe Phe Leu Ala Asn Val Leu Arg Ala Leu Gly Gly Pro
305                 310                 315                 320

Ser Leu Val Pro Gly Pro Ala Phe Leu Ala Leu Asn Trp Leu Gly Tyr
                    325                 330                 335

Ala Asn Ser Ala Phe Asn Pro Leu Ile Tyr Cys Arg Ser Pro Asp Phe
                    340                 345                 350

Arg Ser Ala Phe Arg Arg Leu Leu Cys Arg Cys Gly Arg Arg Leu Pro
                    355                 360                 365

Pro Glu Pro Cys Ala Ala Ala Arg Pro Ala Leu Phe Pro Ser Gly Val
                    370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
                    405

(2) INFORMATION FOR SEQ ID NO: 3:

(i) SEQUENCE CHARACTERISTICS:
        (A) LENGTH: 3437 bases
        (B) TYPE: nucleic acid
        (C) STRANDEDNESS: single
        (D) TOPOLOGY: linear (xi) SEQUENCE DESCRIPTION: SEQ ID NO: 3:

GATCTGTAAT CCCAGCACTG GGAGGTTGA GGCAGAAGGA TCTGGAGGTC              50

CAGACCAATC TGGGCAACAT ATAGAAAGAC TATCTCAAAC AATAAGATAC            100

CTTAGGGAGA GCATCCAAGC AGAAGAGGGG CTATCTTGGA TGGTTTGGGT            150

TGTTCGGTTT TGTTTTGGTT TGTTTCTGGA TGGTTGCCTT CCTTGTTGGG            200

TAAAGGATAG GGTGCGGGGG TTTCTCTTCT TTGCAGGGTT GCCTCAGGTT            250

CTGCCAGGAA GGAGCTGCTG AGCTCCAGGA AACCGGTGCT GAGGGAGTGT            300

CAAGACAGGA CGCCCCTCTC CACCCTCCAA TTCCCACCAG AGGCCTCTCT            350

TGTGACTATT GGACGCTGTT CCTTTAAAAG CAGCCACTCC TCCCGGCAAC            400

TAGGGTGTAC ATGGGGGGTG AGATGGAGGG AAGCTGACAG ACTTACCCCA            450

GCAATTAGGG AAGATGGCCC AGGCTGGAAG AGTCGCTCCC AAGCCCTACT            500

GTCCCCTTCC CTAAGCCAGC GGGTCTGGGG AGGAGGGGGA ACCTTCCCAC            550

CCCAGGCGCC ACACGAGATG GCTCCGTGGC CTCACAGAAA CGGCTCTCTG            600

GCTTTGTGGT CGGACGCCCC TACCCTGGAC CCCAGTGCAG CCAACACCAG            650

TGGGTTGCCA GGAGTACCAT GGGCAGCGGC ATTGGCTGGG GCATTGCTGG            700

CGCTGGCCAC GGTGGGAGGC AACCTGCTGG TAATCATAGC CATCGCCCGC            750
```

-continued

| | |
|---|---|
| ACGCCGAGAC TACAGACCAT AACCAACGTG TTCGTGACTT CACTGGCCGC | 800 |
| AGCTGACTTG GTAGTGGGAC TCCTCGTAAT GCCACCAGGG GCCACATTGG | 850 |
| CGCTGACTGG CCATTGGCCC TTGGGCGAAA CTGGTTGCGA ACTGTGGACG | 900 |
| TCAGTGGACG TGCTCTGTGT AACTGCTAGC ATCGAGACCT TGTGCGCCCT | 950 |
| GGCTGTGGAC CGCTACCTAG CTGTCACCAA CCCTTTGCGT TACGGCACGC | 1000 |
| TGGTTACCAA GCGCCGCGCC CGCGCGGCAG TTGTCCTGGT GTGGATCGTG | 1050 |
| TCCGCTGCCG TGTCCTTTGC GCCCATCATG AGCCAGTGGT GGCGTGTAGG | 1100 |
| GGCAGATGCC GAGGCACAGG AATGCCACTC CAATCCGCGC TGCTGTTCCT | 1150 |
| TTGCCTCCAA CATGCCCTAT GCGCTGCTCT CCTCCTCCGT CTCCTTCTAC | 1200 |
| CTTCCCCTCC TTGTGATGCT CTTCGTCTAT GCTCGAGTGT TCGTTGTGGC | 1250 |
| TAAGCGCCAA CGGCATTTGC TGCGCCGGGA ACTGGGCCGC TTCTCGCCCG | 1300 |
| AGGAGTCTCC GCCGTCTCCG TCGCGCTCTC CGTCCCCTGC CACAGGCGGG | 1350 |
| ACACCCGCGG CACCGGATGG AGTGCCCCCC TGCGGCCGGC GGCCTGCGCG | 1400 |
| CCTCCTGCCA CTCCGGGAAC ACCGCGCCCT GCGCACCTTA GGTCTCATTA | 1450 |
| TGGGCATCTT CTCTCTGTGC TGGCTGCCCT TCTTCCTGGC CAACGTGCTG | 1500 |
| CGCGCACTCG CGGGGCCCTC TCTAGTTCCC AGCGGAGTTT TCATCGCCCT | 1550 |
| GAACTGGCTG GGCTATGCCA ACTCCGCCTT CAACCCGGTC ATCTACTGCC | 1600 |
| GCAGCCCGGA CTTTCGCGAC GCCTTCCGTC GTCTTCTGTG TAGCTACGGT | 1650 |
| GGCCGTGGAC CGGAGGAGCC ACGCGCAGTC ACCTTCCCAG CCAGCCCTGT | 1700 |
| TGAAGCCAGG CAGAGTCCAC CGCTCAACAG GTAGGGGACA CGAGCGGGGG | 1750 |
| ACCGGAGTCT CTGGGTGGGG ACGTCTCTGT CTCTATTTTT GAGTTTGGAG | 1800 |
| ATTGGGGGAG GGGAAGATGT AGATGGGGGT GCGGTGTGTG TGTGGGTGGG | 1850 |
| GGGTGGCCTT TGTCTTGAGA GGACAGAAAA GAGGTAGGAA CTAAAACGGG | 1900 |
| CCCTTTCTCT TCTTGGATCC AATCCCTGGG TCTGAAGCAA AAGGGAGGAA | 1950 |
| GGGGATAATT GCGCACCTTA GGACCAGGTG ACCCCCACAG GCAGTTGCTG | 2000 |
| CTCTTCCGGC AGGTTTCTGA CCTCTCTGGT CGCCTCTAGT TTGGGGTTTG | 2050 |
| TTTGTTTTTG TTTGTTTGTT TGTTTGTTTT GTTTTTTTAG TTCCCTTCTT | 2100 |
| CGGGAACCCA GGCATCTCTA TACCTGTCTG GGATATCCAT AGACAGCAAT | 2150 |
| GGACTTCCCT AGTCCTCGGC CTCAGTCCCG CTCTCTCTCA AAGGTTTGAT | 2200 |
| GGCTATGAAG GTGCGCGTCC GTTTCCCACG TGAAGGGCCG TGAAGATCCA | 2250 |
| GCAAGGAAGC TGTGAGTTGG CTTGGAGTTG CTTTCCTCCC TCAGGGACTG | 2300 |
| GATTAGAACT ATAGGGTGGG ACTTGGGGGG GAGGGAGGGT GCAGGATGGA | 2350 |
| CCCTATGGGA TTTGGGGGTG GAGTAGAGGG ATGCGGGAAT GGTCCCTATA | 2400 |
| TCTTTGAAAA GTGAATATGC TTTTCAGGGT TCCTGAATCA CTTCCCTCTT | 2450 |
| CCTTCCAGTG CTTGATCCCC ATCTTCTTGA CTGGTTGCCC CAAGAAATAT | 2500 |
| TGTTTCCGTT TTTGCAGGAC TTCTGGGGAT TTTTTTTTTC CTCCAGAAAG | 2550 |
| ACAAGCAACG GCTATGGATG CAACATTTTT ATAATGCCTT TGATTTCTAC | 2600 |
| TCAGAGTGAG TCCCCTGGAA CCTCAACTCT CCAACGCTCC AGAACCGATG | 2650 |
| ACTAGACCAC GAGGTGTAAG GGAAATCTTA CCAAATGGGT TTCACCGTCC | 2700 |
| TCTCTCTCTT TCCGAGAGAA GTTGTCTAAG ACCCACCTTG AACTTCACTA | 2750 |

-continued

```
CTACCTCAGC AGCTGGGACG GCAGGCCACC TGTGCTTGAC GGCCCTGGGA          2800

GGAGCCCTAT GGCCTTGGAG GCCTGCCAGT CCCTGCCTAT GTTTGTGCTG          2850

TATGCTTAGG GAAAAGAGAG CACCCCTCCC TCCCTTTCTT CCTACTGCTT          2900

TCCTAACCCT GATGATCGAC ATGTTCCTCC ACAAATCACT CTGTCTCCAG          2950

GCTCTGTGTC TCTGGTTAGT TTGAGAGCAG GAATCCAGGA AAAAAAAAAA          3000

GTTTGAGGTT TCATCCCTGT CTCCTCACTA TGGCTCTCTA AGCACCATCT          3050

TGGACCATCT CTCACAATAG GCACAAAACA GCTCTAATCT ACCTCACAGT          3100

TAGGACTTCA AGGTTTGGGG GGGAAATTCC AGGGTTCATA GGAAGAAGTC          3150

AAACTATTGG AATGGGTCCT TTTTCCACTT AAAATCAAAT TAATAAATAT          3200

TATTGAATGT GGTTTGTCCC CTGCTCGCCT TTTCTCTGGG TTTGTTTTCT          3250

TTTCGTGGCC TGCTTGCTGG CTTCCTTGCT CCGAGCTGCG TTTTGACAGG          3300

GGCAGTAAAT TAGGAGTAAT CCTTGCCTCT TTCTTCCTAA TCCTCATCAG          3350

ACACAACCAG AAAGTCTGTC TGTGTAAGTG AGGCAGTCGA GTCTTTGCCT          3400

CGCCTTCCTC CCCACCTTTT CTGAAACTTT TGAGATC                        3437
```

(2) INFORMATION FOR SEQ ID NO: 4:

(i) SEQUENCE CHARACTERISTICS:
        (A) LENGTH: 400 residues
        (B) TYPE: amino acid
        (C) TOPOLOGY: linear (ii) MOLECULE TYPE:
        (A) DESCRIPTION: polypeptide (xi) SEQUENCE DESCRIPTION: SEQ ID NO: 4:

```
Met Ala Pro Trp Pro His Arg Asn Gly Ser Leu Ala Leu Trp Ser Asp
 1               5                  10                  15

Ala Pro Thr Leu Asp Pro Ser Ala Ala Asn Thr Ser Gly Leu Pro Gly
                20                  25                  30

Val Pro Trp Ala Ala Ala Leu Ala Gly Ala Leu Leu Ala Leu Ala Thr
            35                  40                  45

Val Gly Gly Asn Leu Leu Val Ile Ile Ala Ile Ala Arg Thr Pro Arg
        50                  55                  60

Leu Gln Thr Ile Thr Asn Val Phe Val Thr Ser Leu Ala Ala Ala Asp
65                  70                  75                  80

Leu Val Val Gly Leu Leu Val Met Pro Pro Gly Ala Thr Leu Ala Leu
                85                  90                  95

Thr Gly His Trp Pro Leu Gly Glu Thr Gly Cys Glu Leu Trp Thr Ser
            100                 105                 110

Val Asp Val Leu Cys Val Thr Ala Ser Ile Glu Thr Leu Cys Ala Leu
        115                 120                 125

Ala Val Asp Arg Tyr Leu Ala Val Thr Asn Pro Leu Arg Tyr Gly Thr
    130                 135                 140

Leu Val Thr Lys Arg Arg Ala Arg Ala Ala Val Val Leu Val Trp Ile
145                 150                 155                 160

Val Ser Ala Ala Val Ser Phe Ala Pro Ile Met Ser Gln Trp Trp Arg
                165                 170                 175

Val Gly Ala Asp Ala Glu Ala Gln Glu Cys His Ser Asn Pro Arg Cys
            180                 185                 190

Cys Ser Phe Ala Ser Asn Met Pro Tyr Ala Leu Leu Ser Ser Ser Val
```

```
              195                 200                 205
Ser Phe Tyr Leu Pro Leu Leu Val Met Leu Phe Val Tyr Ala Arg Val
    210                 215                 220

Phe Val Val Ala Lys Arg Gln Arg His Leu Leu Arg Arg Glu Leu Gly
225                 230                 235                 240

Arg Phe Ser Pro Glu Glu Ser Pro Pro Ser Pro Ser Arg Ser Pro Ser
                245                 250                 255

Pro Ala Thr Gly Gly Thr Pro Ala Ala Pro Asp Gly Val Pro Pro Cys
                260                 265                 270

Gly Arg Arg Pro Ala Arg Leu Leu Pro Leu Arg Glu His Arg Ala Leu
                275                 280                 285

Arg Thr Leu Gly Leu Ile Met Gly Ile Phe Ser Leu Cys Trp Leu Pro
                290                 295                 300

Phe Phe Leu Ala Asn Val Leu Arg Ala Leu Ala Gly Pro Ser Leu Val
305                 310                 315                 320

Pro Ser Gly Val Phe Ile Ala Leu Asn Trp Leu Gly Tyr Ala Asn Ser
                325                 330                 335

Ala Phe Asn Pro Val Ile Tyr Cys Arg Ser Pro Asp Phe Arg Asp Ala
                340                 345                 350

Phe Arg Arg Leu Leu Cys Ser Tyr Gly Gly Arg Gly Pro Glu Glu Pro
                355                 360                 365

Arg Ala Val Thr Phe Pro Ala Ser Pro Val Glu Ala Arg Gln Ser Pro
370                 375                 380

Pro Leu Asn Arg Phe Asp Gly Tyr Glu Gly Ala Arg Pro Phe Pro Thr
385                 390                 395                 400

(2) INFORMATION FOR SEQ ID NO: 5:

(i) SEQUENCE CHARACTERISTICS:
        (A) LENGTH: 408 residues
        (B) TYPE: amino acid
        (D) TOPOLOGY: linear (ii) MOLECULE TYPE:
        (A) DESCRIPTION: polypeptide (xi) SEQUENCE DESCRIPTION: SEQ ID NO: 5:

Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
                20                  25                  30

Val Pro Trp Glu Ala Ala Leu Ala Gly Ala Leu Leu Ala Leu Ala Val
                35                  40                  45

Leu Ala Thr Val Gly Gly Asn Leu Leu Val Ile Val Ala Ile Ala Trp
    50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
                100                 105                 110

Trp Thr Ser Val Asp Val Leu Cys Val Thr Ala Ser Ile Glu Thr Leu
                115                 120                 125

Cys Ala Leu Ala Val Asp Arg Tyr Leu Ala Val Thr Asn Pro Leu Arg
                130                 135                 140

Tyr Gly Ala Leu Val Thr Lys Arg Cys Ala Arg Thr Ala Val Val Leu
```

-continued

```
            145                 150                 155                 160
Val Trp Val Val Ser Ala Ala Val Ser Phe Ala Pro Ile Met Ser Gln
                        165                 170                 175

Trp Trp Arg Val Gly Ala Asp Ala Glu Ala Gln Arg Cys His Ser Asn
                180                 185                 190

Pro Arg Cys Cys Ala Phe Ala Ser Asn Met Pro Tyr Val Leu Leu Ser
                195                 200                 205

Ser Ser Val Ser Phe Tyr Leu Pro Leu Leu Val Met Leu Phe Val Tyr
            210                 215                 220

Ala Arg Val Phe Val Val Ala Thr Arg Gln Leu Arg Leu Leu Arg Gly
225                 230                 235                 240

Glu Leu Gly Arg Phe Pro Pro Glu Glu Ser Pro Pro Ala Pro Ser Arg
                245                 250                 255

Ser Leu Ala Pro Ala Pro Val Gly Thr Cys Ala Pro Pro Glu Gly Val
                260                 265                 270

Pro Ala Cys Gly Arg Arg Pro Ala Arg Leu Leu Pro Leu Arg Glu His
            275                 280                 285

Arg Ala Leu Cys Thr Leu Gly Leu Ile Met Gly Thr Phe Thr Leu Cys
            290                 295                 300

Trp Leu Pro Phe Phe Leu Ala Asn Val Leu Arg Ala Leu Gly Gly Pro
305                 310                 315                 320

Ser Leu Val Pro Gly Pro Ala Phe Leu Ala Leu Asn Trp Leu Gly Tyr
                325                 330                 335

Ala Asn Ser Ala Phe Asn Pro Leu Ile Tyr Cys Arg Ser Pro Asp Phe
                340                 345                 350

Arg Ser Ala Phe Arg Arg Leu Leu Cys Arg Cys Gly Arg Arg Leu Pro
            355                 360                 365

Pro Glu Pro Cys Ala Ala Ala Arg Pro Ala Leu Phe Pro Ser Gly Val
            370                 375                 380

Pro Ala Ala Arg Ser Ser Pro Ala Gln Pro Arg Leu Cys Gln Arg Leu
385                 390                 395                 400

Asp Gly Ala Ser Trp Gly Val Ser
                405
```

(2) INFORMATION FOR SEQ ID NO: 6:

(i) SEQUENCE CHARACTERISTICS:
        (A) LENGTH: 400 residues
        (B) TYPE: amino acid
        (D) TOPOLOGY: linear (ii) MOLECULE TYPE:
        (A) DESCRIPTION: polypeptide (xi) SEQUENCE DESCRIPTION: SEQ ID NO: 6:

```
Met Ala Pro Trp Pro His Arg Asn Gly Ser Leu Ala Leu Trp Ser Asp
1                   5                   10                  15

Ala Pro Thr Leu Asp Pro Ser Ala Ala Asn Thr Ser Gly Leu Pro Gly
                20                  25                  30

Val Pro Trp Ala Ala Ala Leu Ala Gly Ala Leu Leu Ala Leu Ala Thr
            35                  40                  45

Val Gly Gly Asn Leu Leu Val Ile Ile Ala Ile Ala Arg Thr Pro Arg
        50                  55                  60

Leu Gln Thr Ile Thr Asn Val Phe Val Thr Ser Leu Ala Ala Ala Asp
65                  70                  75                  80

Leu Val Val Gly Leu Leu Val Met Pro Pro Gly Ala Thr Leu Ala Leu
```

```
                     85                  90                  95
Thr Gly His Trp Pro Leu Gly Glu Thr Gly Cys Glu Leu Trp Thr Ser
                100                 105                 110

Val Asp Val Leu Cys Val Thr Ala Ser Ile Glu Thr Leu Cys Ala Leu
            115                 120                 125

Ala Val Asp Arg Tyr Leu Ala Val Thr Asn Pro Leu Arg Tyr Gly Thr
        130                 135                 140

Leu Val Thr Lys Arg Arg Ala Arg Ala Ala Val Val Leu Val Trp Ile
145                 150                 155                 160

Val Ser Ala Ala Val Ser Phe Ala Pro Ile Met Ser Gln Trp Trp Arg
                165                 170                 175

Val Gly Ala Asp Ala Glu Ala Gln Glu Cys His Ser Asn Pro Arg Cys
            180                 185                 190

Cys Ser Phe Ala Ser Asn Met Pro Tyr Ala Leu Leu Ser Ser Ser Val
        195                 200                 205

Ser Phe Tyr Leu Pro Leu Leu Val Met Leu Phe Val Tyr Ala Arg Val
    210                 215                 220

Phe Val Val Ala Lys Arg Gln Arg His Leu Leu Arg Arg Glu Leu Gly
225                 230                 235                 240

Arg Phe Ser Pro Glu Glu Ser Pro Pro Ser Pro Ser Arg Ser Pro Ser
                245                 250                 255

Pro Ala Thr Gly Gly Thr Pro Ala Ala Pro Asp Gly Val Pro Pro Cys
            260                 265                 270

Gly Arg Arg Pro Ala Arg Leu Leu Pro Leu Arg Glu His Arg Ala Leu
        275                 280                 285

Arg Thr Leu Gly Leu Ile Met Gly Ile Phe Ser Leu Cys Trp Leu Pro
    290                 295                 300

Phe Phe Leu Ala Asn Val Leu Arg Ala Leu Ala Gly Pro Ser Leu Val
305                 310                 315                 320

Pro Ser Gly Val Phe Ile Ala Leu Asn Trp Leu Gly Tyr Ala Asn Ser
                325                 330                 335

Ala Phe Asn Pro Val Ile Tyr Cys Arg Ser Pro Asp Phe Arg Asp Ala
            340                 345                 350

Phe Arg Arg Leu Leu Cys Ser Tyr Gly Gly Arg Gly Pro Glu Glu Pro
        355                 360                 365

Arg Ala Val Thr Phe Pro Ala Ser Pro Val Glu Ala Arg Gln Ser Pro
    370                 375                 380

Pro Leu Asn Arg Phe Asp Gly Tyr Glu Gly Ala Arg Pro Phe Pro Thr
385                 390                 395                 400

(2) INFORMATION FOR SEQ ID NO: 7:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (xi) SEQUENCE DESCRIPTION:  SEQ ID NO: 7:

GCTCCGTGGC CTCACGAGAA                                                   20

(2) INFORMATION FOR SEQ ID NO:  8:

(i) SEQUENCE CHARACTERISTICS:
        (A) LENGTH:  25 bases
        (B) TYPE:  nucleic acid
        (C) STRANDEDNESS:  single
```

-continued

```
        (D) TOPOLOGY:  linear (xi) SEQUENCE DESCRIPTION:  SEQ ID NO: 8:

CCCAACGGCC AGTGGCCAGT CAGCG                                            25

(2) INFORMATION FOR SEQ ID NO: 9:

(i) SEQUENCE CHARACTERISTICS:
         (A) LENGTH:  36 bases
         (B) TYPE:  nucleic acid
         (C) STRANDEDNESS:  single
         (D) TOPOLOGY:  linear (xi) SEQUENCE DESCRIPTION:  SEQ ID NO: 9:

CTGGTCCAGG GGAGGGGACA                                                  20

GCAAGGCATG AGAGCG                                                      36
```

INTRON/EXON OF THE HUMAN AND MOUSE BETA 3-ADRENERGIC RECEPTOR GENES

This application is a divisional of application Ser. No. 08/117,829, filed Sep. 8, 1993, now abandoned, which is a CIP of Ser. No. 07/721,571, filed Sep. 3, 1991, now U.S. Pat. No. 5,288,607.

BACKGROUND OF THE INVENTION

The present invention relates to the entire gene encoding β3-adrenergic receptor polypeptides of mouse and human origin, which polypeptides provide a procedure for studying the effects of various chemical agents on the β3-adrenergic receptor and coupled adenylate cyclase and hormone-sensitive lipases. More particularly, the present invention also relates to antibodies, vectors, nucleotide probes, cell hosts transformed by genes encoding polypeptides, having β3-adrenergic receptor activity.

In the past, two main classes of adrenergic receptors have been identified as the a adrenergic receptors and the β adrenergic receptors. These adrenergic receptors produce various responses to effector organs such as the eye, heart, arteriols, veins, lungs, stomach, intestine, gallbladder, kidney, skin, spleen, liver and pancrease to mention a few. These specific receptors have been defined by the effects of particular synthetic agonists which stimulate the receptors biological function and antagonists which block the adrenergic receptors biological function.

Within the two classes of adrenergic receptors, four subtypes, α1, α2, β1 and β2, of these receptors for catecholamines have been identified. See, Cotecchia et al., P.N.A.S., 85, pgs. 7159–7163 (1988); Kobilka et al., *Science* 238, pgs. 650–656 (1987); Frielle et al., P.N.A.S., 84, pgs. 7920–7924 (1987); and Emorine et al., P.N.A.S., 84, pgs. 6995–6999 (1987). Drugs that selectively block or stimulate one of these receptor subtypes are used extensively in clinical medicine. Despite the efficacy of these drugs, many produce side effects in individuals, due to their interaction with other receptor subtypes. For identification of the various drugs which act on the receptor subtypes, see Goodman and Gilman's *The Pharmacological Basis of Therapeutics,* eigth edition, MacMillan Publishing Co., Inc. (1990).

The analysis of the genes of these receptors indicate that all of the subtypes of the receptors belong to the family of integral membrane receptors exhibiting striking homologies, in particular these homologies are present in the 7 transmembrane regions. These receptors are coupled to regulatory proteins termed G proteins which are capable of binding molecules of guanosine triphosphate (GTP).

The G proteins have the capacity to intervene structurally and functionally between receptors and enzymes catalyzing the production of intracellular mediators such as adenylate cyclase, guanylate cyclase, the phospholipases and the kinases, or between receptors and ion channels. Thus, the G proteins have the capacity to regulate the flux of ions such as calcium, potassium, sodium and hydrogen ions.

The above-mentioned subtypes of receptors are known in the art as the "R$_7$G family" as described by Emorine et al. Proc. NATO Adv. Res. Workshop (1988). The R$_7$ family comprises acetylcholine muscarinic receptors, serotonin receptors, the receptors for neuropeptides, substance K, angiotensin II and the visual receptors for the opsins, as described by Dixon et al *Annual Reports in Medicinal Chemistry,* pgs. 221–233 Ed. Seamon, K. B., Food and Drug Administration, Bethesda, Md. (1988) and Emorine et al., supra.

Recently, a third subtype of the β-adrenergic receptor termed β3-adrenergic receptor, has been identified and characterized in humans and in rodents, which polypeptide does not have a receptor activity similar to that of the β1- or β2-adrenergic receptors. This "new" β3-receptor in humans has been identified and sequenced as described in French application No.8900918 filed Jan. 25, 1989 and PCT/FR90/00054, resulting in U.S. application Ser. No.07/721,571, filed Jan. 25, 1990, U.S. Pat. No. 5,288,607, incorporated herein by reference, as containing 402 amino acids, which is capable of activating adenylate cyclase in the presence of an agonist, which activity increases in the order of agonists of salbutamol, BRL 28410, BRL 37344 and (1)-isoproterenol. Antibodies directed to the polypeptide of the β3-adrenergic receptor were also disclosed. The β3-receptor was identified as differing from the β1-adrenergic receptor and the β2-adrenergic receptor by a pharmacological comparison of the activation of adenylate cyclase in the presence of agonists and the reaction towards different antagonists.

Similarly, the β3-adrenergic receptor of the mouse has been identified and cloned as described in French application No. 9100320 filed Jan. 14, 1991 and PCT/FR92/00023 filed Jan. 15, 1992, also incorporated herein by reference. See also, Nahmias et al., *Embo J.,* 10, pgs. 3721–3727 (1991). The mouse β3-adrenergic receptor encodes a polypeptide of 388 amino acid residues, including the features characteristic of β-adrenergic receptors, such as the conserved amino acids identified as crucial for catecholamine binding in the β2-adrenergic receptor. See, Strader et al., *FASEB J.* 3, pgs. 1825–1832 (1989).

A pharmacological comparison of the mouse with the human counter part of the β3-adrenergic receptors indicates that these receptors have similar reactivity. For example, mouse β3-adrenergic receptor can be activated by CGP 12177A, oxprenolol and pindolol while displaying a low stereoselectivity and characteristic potency order for full agonists, which is similar to the human.

However, differences do exist between the mouse β3-adrenergic receptor and the human β3-adrenergic receptor, which are probably due to the structural differences observed between these two receptors in the transmembrane domains which are involved in ligand binding wherein 12 substitutions do occur.

Thermogenesis and lipolysis in brown and white adipose tissues are under the control of this β3-adrenergic receptor subtype as described by Arch et al., *Proc. Nutr. Sci.,* 48, pgs. 215–223 (1989); Arch et al., *In Obesity,* John Wiley & Sons Ltd., London (1991); and Zaagsma et al., *Trends Pharmacol. Sci.,* 11, pgs. 3–7 (1990). Besides adipose tissues, the expression of the β3-adrenergic receptor has also been reported in various other tissues such as tissues of the digestive tract, from oesophagus to colon and in the gallbladder. See, for example, Bond et al., *Br. J. Pharmacol.,* 95, pgs. 723–734 (1988); Coleman et al., *British Journal of Pharmacology Proc. Supl.,* 90, 40 (1987); Bianchetti et al., *Br. J. Pharmacol.,* 100, pgs. 831–839 (1990); Granneman et al., *J. Pharmacol. Exp. Ther.,* 256, pgs. 421–425 (1991); and Krief et al., *J. Clin. Invest.,* (1993) (in press). This β3-adrenergic receptor subtype has been suggested to participate in the control by catecholamines of body energy balance from intestine assimilation to storage and mobilization in adipose tissue.

Factors such as temperature, feeding or fasting and stress influence the body's hormonal status, thus inducing tissue specific adaptive modifications of energy balance which may in part result from regulation of cellular β3-adrenergic receptor sensitivity. It has been further shown that β-adrenergic agonists, glucocorticoids and several other agents can modulate β3-adrenergic receptor density, responsiveness and mRNA levels. The molecular determinants responsible for the regulation of cellular β3-adrenergic receptor may possibly be found either on the receptor itself or in its gene or mRNA. For example, post-translational modifications of the receptor in the third intra-cytoplasmic loop or in the carboxy-terminal tail may modulate β-adrenergic receptor coupling to adenylate cyclase. Factors which act on β-adrenergic receptor gene transcription rate or on mRNA stability may also modulate cellular adrenergic responsiveness by modifying β-adrenergic receptor expression levels.

The β3-adrenergic receptors have been sequenced and identified, as well as compared pharmacologically with other known receptors in mouse and humans. A comparison of the β3-adrenergic receptor amino acid sequences predicted from the nucleotide sequences of the human and mouse genomic genes revealed differences in the carboxy-terminal regions of the receptors. Although these differences could be attributed to evolutionary species-related variations, it was recently discovered by the present inventors that the entire coding sequence for the previously reported β3-adrenergic receptor in mouse and human was not complete. The genes encoding β1- and β2- comprise one exon and it was thought that the β3-adrenergic receptor gene, when initially identified, also comprised only one exon. However, it was recently and unexpectedly discovered that contrary to β1- and β2-adrenergic receptor genes, the human and mouse β3-adrenergic receptor genes comprise several exons. The identification of the introns and exons in mouse and human β3-adrenergic receptors and thus the entire gene itself, permits a full characterization of this receptor which will aid in more sensitive genetically engineered products such as nucleotide probes, polyclonal and monoclonal antibodies and the like for drug testing and diagnostic purposes, and permits the understanding of β3-adrenergic receptor regulated expression in various tissues.

SUMMARY OF THE PRESENT INVENTION

Thus, it is an object of the present invention to provide polypeptides having β3-adrenergic receptor activity in mammals which polypeptides encode the entire human and mouse β3-adrenergic receptor genes.

A specific object of the present invention is to provide the entire amino acid and nucleotide sequences, as well as the intron/exon organization for the human and mouse β3-adrenergic receptor which molecule characterizations are useful in not only detecting the β3-adrenergic receptor in different species, but also testing new drugs for regulating β3-adrenergic receptor activities.

Yet another object of the present invention is to provide nucleotide probes capable of hybridizing to the genes encoding the polypeptides having β3-adrenergic activity in mammals for detecting this receptor in different mammalian species and for measuring the variations in the levels of expression of the β3-receptor in mammalian cells.

Another object of the present invention is to provide antibodies, polyclonals and monoclonals which recognize the entire sequence of the β3-adrenergic receptor in mammals, which antibodies do not recognize the β1-adrenergic receptor or β2-adrenergic receptor for detecting and diagnostic purposes.

A further object of the present invention is to provide recombinant vectors for the cloning and expression of β3-adrenergic receptor proteins in mammals.

Another object of the present invention is to provide a cell host which comprises the elements of regulation making possible the expression of the nucleotide sequence encoding the polypeptides of β3-adrenergic receptors in mammals.

BRIEF DESCRIPTION OF THE DRAWINGS

FIG. 1 depicts the nucleotide sequence (SEQ ID NO:1), amino acid translation (SEQ ID NO:2) and intron/exon organization of the human β3-adrenergic receptor gene.

FIG. 2 depicts the nucleotide sequence (SEQ ID NO:3), amino acid translation (SEQ ID NO:4) and intron/exon organization of the mouse β3-adrenergic receptor gene.

FIG. 3 is the complete amino acid sequence (SEQ ID NO:5) for the human β3-adrenergic receptor.

FIG. 4 is the complete amino acid sequence (SEQ ID NO:6) for the mouse β3-adrenergic receptor.

DESCRIPTION OF THE PREFERRED EMBODIMENTS

Figure 5B:
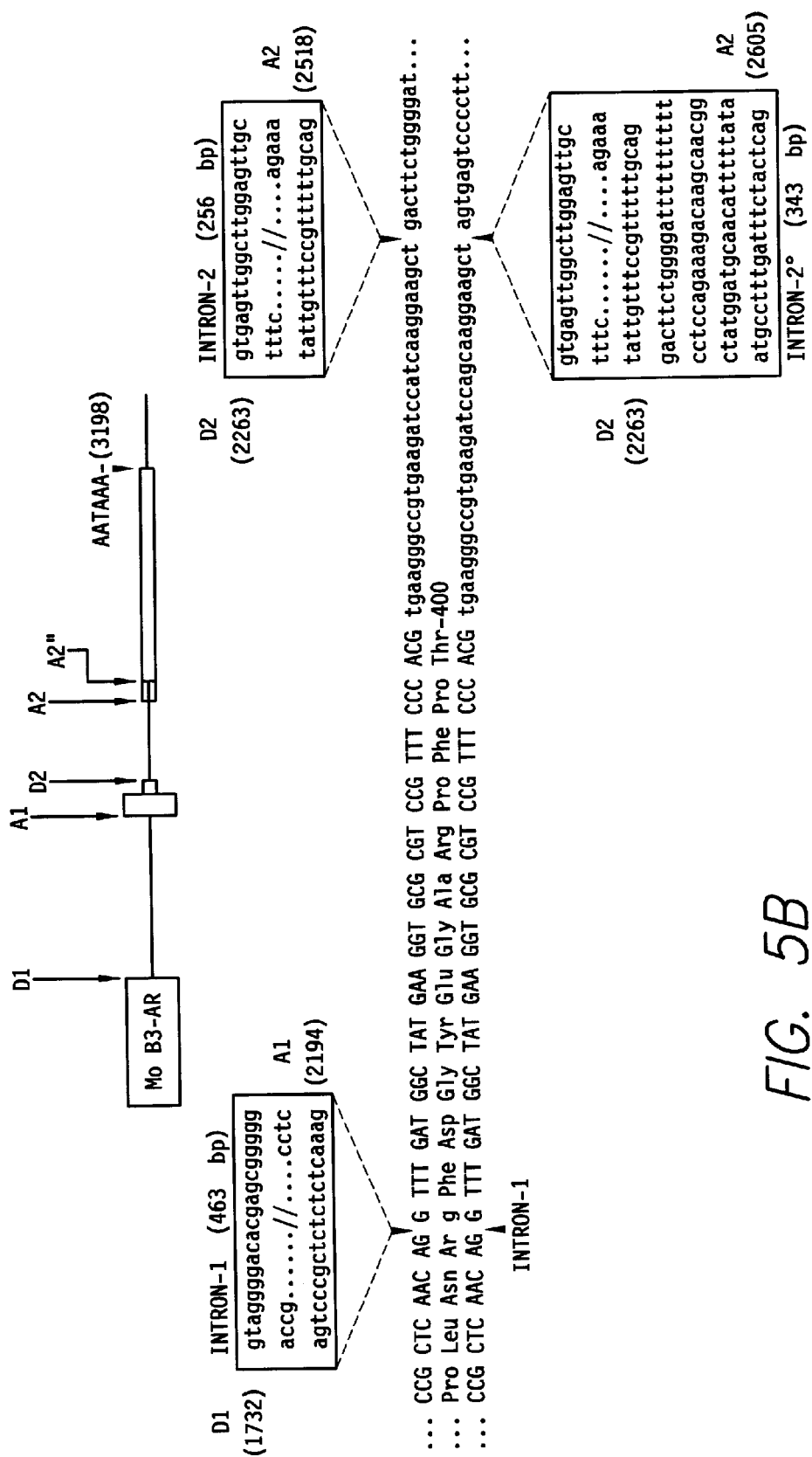
FIG. 5 is a schematic representation of human and mouse β-adrenergic receptor mRNA splicing.

In particular, the present invention provides various genetically engineered products such as nucleotide probes, monoclonal and polyclonal antibodies for testing a variety of chemical agents including drugs, ligands and the like which may influence the regulation of β3-adrenergic receptors. Moreover, in this testing method, it is of importance to have the entire sequence of the β3-receptor gene, since elements in the promoter region, in the intron/exon region and in the 3' untranslated region may influence the expression of β3. By testing drugs that may increase and/or decrease the expression levels of the β3-adrenergic receptor, various diseases such as obesity, diabetes and hyperlipidemia and the like, may be controlled.

Accordingly, the present invention also provides a method for in vitro diagnosis of energy-balance related diseases which diseases can be diagnosed by abnormalities in β3-adrenergic receptor activity.

The present invention also provides vectors containing genes coding for polypeptides having β3-adrenergic receptor activity in mammals, as well as cell hosts transformed by genes coding for the above-mentioned polypeptides.

By mammals is meant any class of higher vertebrates comprising man and all other animals that nourish their young with milk secreted by mammary glands and have skin, usually more or less covered by hair, including monkeys, mice, rat, humans and the like.

Any mammalian polypeptide displaying β3-adrenergic receptor activity is a part of the present invention, but preferable polypeptides encoding the amino acid sequences set forth in FIGS. 3 (SEQ ID NO:5) and 4 (SEQ ID NO:6).

Variations of the polypeptides is also encompassed by the present invention provided that these variant polypeptides do not lose β3-adrenergic receptor activity. Any technique known in the art may be used to provide these variant polypeptides including nucleotide-mediated mutagenesis, oligonucleotide-mediated "loop out" mutagenesis, linker-inserted mutagenesis and the like. These methods are well-known and described, for example by Sambrook et al. in *Molecular Cloning A Laboratory Manual,* second edition, Cold Spring Harbour Laboratory Press (1989).

Besides polypeptides, the present invention also encompasses any nucleotide sequence of β3-adrenergic receptors in mammals. A preferred embodiment of these nucleotide sequences are encompassed in FIGS. 1 (SEQ ID NO:1) and 2 (SEQ ID NO:3). Variants of the nucleotide sequence are also encompassed in the present invention including mutations and point substitutions using the above-described mutagenesis methods, provided that these variations do not significantly alter β3-adrenergic receptor activity.

These nucleotides can be prepared by any synthesis method known in the art. Examples of these methods include, but are not limited to the automated β-cyanoethyl phosphoramidite method described in *Bioorganic Chemistry*, 4, pgs. 274–325 (1986) which method is suitable for the preparation of a nucleotide sequence containing a maximum of 200 nucleotides and those described in P.N.A.S., 80, pgs. 7461–7465 (1983) for nucleotides longer than 200.

Besides synthesis of nucleotides, the present invention also relates to the purification of nucleotides from genomic DNA or cellular RNA from any mammalian tissue expressing the β3-adrenergic receptor including adipose, muscular, hepatic, intestinal, gallbladder tissues and the like. mRNA can then be isolated and cDNA synthesized therefrom by the methods described in Sambrook et al. *Molecular Cloning*, supra.

The nucleotide sequences or fragments thereof can be cloned and/or expressed in a plasmid, cosmid or phage type vector. Thus, the present invention also includes recombinant vectors which which can be use to clone or express in a variety of host microorganisms the β3-adrenergic receptor. Various vectors include, but are not limited to pBr322, pUC18/pUC19, pUC119, p5P64/p5P65, pGEM-3/pGEM-4, pGEM-3Z, πAN13, Bluescript M13, λgt10, λ2001, λDASH, λFIX, C2RB, pWE15 and the like.

A preferred vector includes a HindII-PstI fragment of genomic DNA derived from mouse having about 5.5 kilobases and containing the totality of the gene coding for the β3-adrenergic receptor in mouse including the promoter region and Exon 1, Exon 2 and Exon 3, which fragment was inserted into a HindII-PstI site of pUC18. The plasmid was transformed in *E. coli*(JM101). This vector, (030 B315-I) was deposited under the No. I-1272 on Dec. 1, 1992 with the C.N.C.M., Collection Nationale de Cultures de Microorganismes, 25 rue du Docteur Roux, Paris France.

A second preferred vector includes a BglII fragment of genomic DNA derived from humans having about 4.5 kilobases and containing the totality of the gene coding for the β3-adrenergic receptor in humans including the promoter region and Exon 1 and Exon 2, which fragment was inserted into a BamHI site of pUC18. The plasmid was then transformed in *E. coli* (JM101). This vector, (119 B315-III) was deposited under the No. I-1273 on Dec. 1, 1992 with the C.N.C.M., Collection Nationale de Cultures de Microorganismes, 25 rue du Docteur Roux, Paris France.

For expression the vector contains in at least one of its sites not essential for replication, elements necessary to promote the expression of the polypeptide of the present invention in a cell host. For example, a promoter recognized by the RNA polymerase of the cell host may be used. Any promoter that accomplishes expression can be used, but it is preferable to use an inducible promoter and if necessary, a signal and an anchoring sequences. For expression in eukaryotic cells, the regulatory elements may include the endogenous promoter for the adrenergic receptors or viral promoters such as those of SV40 virus or Rous Sarcoma virus, while for bacterial expression, the regulatory elements may include the lactose operon, the tryptophan operon and the like.

Cell hosts transformed by any of the above-described vectors are also encompassed by the present invention. Any cell host capable of expressing any mammalian β3-adrenergic receptor polypeptide or fragments thereof is encompassed by the present invention. These cell hosts include any eukaryotic or prokaryotic cells including bacteria such as *E. coli*, yeast, CHO cells and the like. It is of interest to note that when the entire intron/exon sequence of the mouse or human β3-adrenergic receptor is expressed in a variety of eukaryotic cell hosts including CHO and L-cells, splicing of the gene takes place correctly.

The recombinant vectors and cell hosts transformed with these vectors are useful tools to generate with ease and facility various nucleotide probes.

These nucleotide probes can also be prepared from the nucleotide sequences, as discussed above, via synthesis and purification techniques and then labelled with a detectable marker. Any detectable marker can be used to label the specific nucleotide sequence of interest, such as $^{14}C$, $^{32}P$, enzyme markers and the like. The labelling conditions for the sequences are well known in the art and for reference such techniques described by Sambrook et al. *Molecular Cloning*, supra may be used.

More particularly, it is advantageous to use a full length probe having the nucleotide sequence as defined in FIGS. 1 (SEQ ID NO:1) and 2 (SEQ ID NO:3) to probe a genomic or cDNA library of different mammalian species to obtain the related β3-adrenergic receptor of interest. A fragment of the nucleotide probe can also be generated.

A nucleotide probe is also useful in measuring the variations in the levels of expression of the β3-adrenergic receptor in mammalian cells, since altered levels of expression may result in specific abnormalities in various mammalian tissues. More specifically, the nucleotide probes may be produced such that they react with specific sequences of the β3-adrenergic receptor gene. Thus, even if this receptor is present in the specific species of mammals being tested, the ligand binding sites or other functional regions in the sequence may contain an abnormality that can be ascertained by the use of such probes.

The nucleotide probes which are suitable for use in the present invention include DNA probes, RNA probes, synthetic oligonucleotide probes, thioester probes and the like. Tandem probes may also be used. The tandem probes may be constructed by covalently joining two or more type-specific β3-adrenergic receptor nucleotide sequences within a single vector. A mixture of the above-mentioned probes is also contemplated for detection purposes.

The conditions required for hybridization and washing of the oligonucleotide probes for detecting the presence of the β3-adrenergic receptor may be different depending on the type of probe utilized. Empirically determined formulae available in the literature allow for the estimation of the oligonucleotide dissociation temperature. Hybridization of oligonucleotides also depend on several factors, which include the length of the probe and the GC content. The hybridization conditions, thus will be adjusted according to the probes used and are well within a person skilled in the art's knowledge.

The labelled hybrids are then detected depending on the type of labelled probe used. For example, an enzymatically labelled probe will require enzymatic detection, while if a radioactive label is used, gamma or beta counters or autoradiography may be used.

The present invention also relates to antibodies directed against the polypeptides of the β3-adrenergic receptor in mammals. These antibodies are specific for the β3-adrenergic receptor and not the β1- nor β2-adrenergic receptors. These antibodies may be produced by injecting the β3-adrenergic receptor protein or polypeptide thereof into an animal. The antibodies generated by the immune response may be recovered and purified by methods known in the art. Besides their use for detection and in vitro diagnostic purposes, the antibodies of the present invention may also be used to purify related receptors in semi-purified form by their attachment to a solid support such as gel beads.

Monoclonal antibodies may be produced by the known method described by Kohler and Milstein, *Nature,* 256, page 495 (1975). These antibodies are useful to diagnose the amount and the presence of the β3-adrenergic receptor in a variety of mammalian species. Thus, the quantity and presence of this receptor may be important to diagnose diseases related to energy abnormalities in a variety of mammalian tissues.

Although direct detection of the β3-adrenergic receptor polypeptide is possible by the use of genetically engineered products as described above, these products are not limited in use to only detecting the presence of β3-receptors in various species. Testing of different drugs for the treatment of obesity, fatty diabetes, hyperlipidemias and the like are within the scope of the present invention by use of the aforementioned nucleotide probes, β3-adrenergic receptors and anti-receptor antibodies.

A procedure for studying the affinity of a β3-adrenergic receptor polypeptide for one or more chemical agents such as drugs, ligands and the like is also encompassed by the present invention.

To study the effects of various chemical agents, a cultured transformed host cell having a sequence encoding the entire β3-adrenergic receptor gene under conditions allowing the expression of such gene is performed. The expression product, which may be exposed at the surface of the transformed cell host or present in the cytoplasm of the host cell, is then utilized to test a variety of ligands, drugs and chemical agents by placing these agents in contact with the transformed cell host. An affinity reaction between the transformed cell host and the specific agent is then detected.

The transformed host cells containing the polypeptide sequence of the β3-adrenergic receptor can also be used to test intracellular responses to various chemical agents.

More specifically, it is known in the art that a variety of hormones, both peptidic and non-peptidic, exert their cellular effects through interaction with cell surface receptors coupled to guanine nucleotide binding proteins or the G-proteins. The G-protein coupled receptors mediate a variety of intracellular responses, wherein the initial specificity is usually determined at the level of the cell surface receptor. The diversity of the cellular responses results from the differential coupling of the receptor to various G-proteins, each of which stimulates a distinct intracellular effector system. The G-protein linked receptor can bind a variety of agonists which stimulates the G protein coupled to the receptor. The activation of the stimulatory G protein leads in turn to adenylate cyclase stimulation and thus an increase in cAMP levels in cells. The β3-adrenergic receptor has the ability to couple G protein and thus the effects of various agonists to activate the stimulatory G protein, raising cAMP levels in the cell can also be tested using the transformed cell hosts of the present invention.

It is of extreme importance that the entire gene sequence be utilized to conduct the above-identified studies, since it is known that the additional sequences described in the present invention effect the regulation of these receptors and especially influence the receptor's expression. Thus, for instance, to test specific ligands and drugs which may aid in an agent to reduce obesity (since the β3-adrenergic receptor is present in low quantities in obese patients) it may be necessary to increase the amount of β3-receptor present. The RNA expression levels of the β3-adrenergic receptor may be regulated by additional sequences described and characterized in the present invention such as the sequences present in the promoter region, the intron/exon region and the 3' untranslated region. Thus, an agent that can be found to increase the transcription of β3-receptors may lead to treatment for obesity and diabetes.

The cloning and initial sequencing of the human and mouse β3-adrenergic receptor genomic genes have been previously described. Nahmias et al., *THE EMBO JOURNAL* vol. 16, No. 12 pgs. 3721–3727 (1991) and Emorine et al., *Science* vol. 245, pgs. 1118–1121 (1989). Both of these references are incorporated herein by reference. To obtain more insight into the mechanisms at the basis of the regulated expression of the β3-adrenergic receptor in both human and mouse, further study was undertaken. By comparing the β3-adrenergic receptor gene and the PCR-amplified cDNA sequences, the presence of introns which interupted the coding and the 3'-untranslated regions of the human and mouse β3-adrenergic receptor gene was discovered.

Nucleotide sequencing was performed on a 2.5 kb SphI-BglII fragment spanning the entire 3'-untranslated regions of the human gene and a 2.2 kb XhoI-BglII fragment spanning the entire 3' untranslated region of the mouse β3-genomic genes after insertion of these fragments in both orientations into M13 cloning vectors. Individual subclones were then sequenced by the standard chain termination method. The primers used were oligonucleotides synthesized step by step during the course of the sequence determination.

A preferred embodiment of the present invention is the identification of two exons in humans and three exons in mice, which contain the entire β3-adrenergic receptor gene sequence. In humans, a large 1.4 kb exon encodes the first 402 amino acid residues, while the second exon of 700 base pairs encodes the sequence for the six carboxy-terminal residues of β3-adrenergic receptor, as well as the entire untranslated 3' region of the β3-adrenergic receptor mRNA.

In mice, there are three exons. The first exon encodes 388 amino acid residues of the β3-adrenergic receptor; a second exon of 68 base pairs encodes for the twelve carboxy-terminal residues of the β3-adrenergic receptor and the third exon of about 600 to 700 base pairs with two acceptor splice sites codes for the 3'-untranslated region of β3-adrenergic receptor mRNA. In mouse adipose tissues, alternate splicing at the two splice sites found in the third exon generates two β3-adrenergic transcripts. The shorter transcript is the major transcript found in white adipose tissue, while the longer transcript is slightly predominant in brown adipose tissue.

Thus, the amino acid sequence for human β3-adrenergic receptor is 6 amino acids longer then previously thought, while the mouse sequence is 12 amino acids longer than previously reported. The nucleotide and amino acid sequences as well as the mRNA splicing are depicted in FIGS. 1–5 for the human and mouse β3-adrenergic receptor.

The localization of the mRNA transcription start sites was undertaken by $S_1$ nuclease mapping and the mRNA transcription start sites for both mouse and human β3-adrenergic receptor mRNA were then localized in a region between 150–190 nucleotides upstream from the ATG translation start cocon. In mouse, a second mRNA initiation region exists further upstream. Further upstream from the mRNA cap sites, glucocorticoid response elements were found in the immediate vicinity of recognition sequences for transcription factor AP-1. The inhibitory effects of glucocorticoids on β3-adrenergic receptor mRNA levels may result from interactions of glucocorticoid receptor with c-fos ad c-jun products which constitutes transcription factor AP-1.

Thus, the entire genes including the promoter region, the intron/exon region and the 3'-untranslated region, coding for β3-adrenergic receptors were obtained, as well as the mRNA transcription start sites. This finding is of utmost importance not only for detection and diagnostic purposes, but also to obtain drugs useful in the regulation of β3 expression in tissue. Thus, the utilization of alternate promoters and/or splice sites allows tissue specific regulation of β3-adrenergic expression.

EXAMPLE 1

Isolation and sequencing of the murine β3AR gene

All the methods used for recombinant DNA procedures are from Ausubel et al. *Science* 245, pgs 1118–1121 (1987). A 1.3 kb NcoI-BamHI DNA fragment encompassing the entire coding region of the human β3AR gene (Emorine et al. *Current Protocols in Molecular Biology*, Greene publishing Associates and Wiley InterScience, New York (1989)) was used as a probe to screen a mouse NIH 3T3 genomic library in the lambda FIX™II vector (Stratagene). The nitrocellulose replica filters of the library were prehybridized for 16 h at 42° C. in a buffer containing 8 mM Tris-HCl (pH 7.5), 40% formamide, 4×SSC, 5×Denhardt's, 0.2% SDS, 50 mM sodium phosphate and 100 μg/ml heat-denatured salmon sperm DNA. Hybridization was performed for 16 h at 42° C. in the same buffer containing the probe ($2 \times 10^6$ c.p.m./ml)$^{32}$P-labelled by the random priming method to a specific activity of $10^9$ c.p.m./μg. Final washes were at 45° C. in 0.1×SSC and 0.05% SDS.

A 2 kb BglII-BamHI restriction fragment hybridizing to the probe was subcloned in both orientation into M13mp18. Nested deletions were created with the exonuclease III and sequencing was performed by the dideoxy chain termination method using [α-$^{35}$S]dATP (800 Ci/mmol, Amersham) and *Thermophilus aquaticus* (Taq) polymerase (Taquence kit, USB). Sequence analysis were carried out using the CIT12 (University Paris V, Paris, France) computer software facilities.

EXAMPLE 2

DNA probe and Hybridization Analysis

A 310 bp DNA fragment ("A43") corresponding to the N-terminus of the mouse β3-adrenergic receptor was produced by polymerase chain reaction using a template of 5 ng of the lambda clone containing the mouse β3-adrenergic receptor gene. Thirty cycles of amplification at 93° C. for 1.5 minute; 55° C. for 2 minutes; and 72° C. for 2 minutes were performed using 2.5 U Taq polymerase (Cetus) in 100 μl of buffer containing 10 mM Tris-HCl (pH 8.4), 3 mM MgCl$_2$, 0.05% TWEEN 20, 0.05% NP40, 10% dimethylsuplhoxide, 5% formamide, 125 μM of each deoxynucleotide triphosphate and 125 pM of each primer. Sense (SEQ ID NO:7) (5'-GCTCCGTGGCCTCACGAGAA-3') and antisense (SEQ ID NO:8) (5'-CCCAACGGCCAGTGGCCAGTCAGCG-3') primers corresponding to amino acids 2–8 and 98–106, respectively of the human β3-adrenergic receptor sequence. The amplified 310 bp DNA fragment was purified by electrophoresis through an acrylamide gel. $^{32}$P-labelled by random priming to a specific activity of $10^9$ c.p.m./μg, and used as a probe in Southern and Northern blot experiments.

For Southern blot hybridization analysis, single restriction enzyme digests of genomic DNA (10 μg) were performed and the samples were electrophoresed through a 0.8% agarose gel and blotted onto nylon (Hybond N+, Amersham) filters. Prehybridization and hybridization procedure were performed as described above and final washes were at 45° C. in 0.1×SSC, 0.05% SDS.

For Northern blot analysis, total RNA extracted from mouse or cultured cells was denatured in Glyoxal-DMSO, electrophoresed through a 1% agarose gel and transferred onto a nylon membrane (Hybond N+, Amersham). Prehybridization and hybridization, as well as washing were performed as described above, except that hybridization was performed in the presence of 10% dextran sulphate.

EXAMPLE 3

In situ hybridization

For chromosal localization of the β3-adrenergic receptor gene in mouse, in situ hybridization was performed on metaphase spreads of concavalin A-stimulated lymphocytes from a WMP male mouse, in which all the autosomes except number 19 were in the form of metacentric Robertsonian translocations. For localization of the β3-adrenergic receptor gene in man, metaphase spreads were from phytohaemagglutinin-stimulated human lymphocytes. In both cases the lymphocytes were cultured at 37° C. for 72 hrs., with 5-bromodeoxyuridine (60 μg/ml) added for the final 7 hours of culture.

Specific probes were the 310 bp A43 fragment of the mouse β3-adrenergic receptor gene and a 206 bp (AccI-ApaLI) DNA fragment encompassing the third intracytoplasmic loop of the human β3-adrenergic receptor. These fragments were subcloned into the pUC19 plasmid vector, tritium labelled by nick translation to a specific activity of $10^8$ d.p.m./μg, and used at a final concentration of 25 ng/ml of hybridization solution. Hybridization to metaphase spreads, post-hybridization washes, emulsion autoradiography, R-banding and silver grain analysis were carried out as described by Mattei et al. *HUMAN GENETICS*, 69, pgs. 268–271 (1985).

EXAMPLE 4

Construction, cell culture and transfections

For expression in eukaryotic cells, a 1365 bp NarI-BamHI restriction fragment from the mouse β3-adrenergic receptor gene was inserted under the control of the SV40 early promoter into a plasmid vector containing the 3'-untranslated region of the gene for the hepatitis-B surface antigen, and murine dihydrofolate reductase (DHFR) gene as a selectable marker as described by Larsky et al. *Biotechnology*, 2, pgs. 527–530 (1984). The resulting construct contained 15 bp of 5' untranslated region, 1164 bp of coding region and 186 bp of 3' non-coding region of the mouse β3-adrenergic receptor gene.

CHO cells, deficient in DHFR, were grown in Ham's F12 medium (Seromed) supplemented with 10% fetal calf serum, 2 mM L-glutamine, 15 μg/ml glycine, 9.5 μg/ml hypoxanthine and 1.46 μg/ml thymidine. Transfection with 5 μg of the expression vector was performed by the calcium phosphate precipitation method as described by Tate et al. *EUR. J. Biochem.*, 196, pgs. 357–361 (1991). Stable transformants expressing the DHFR gene were screened for the expression of β adrenergic receptor by stimulation of cAMP accumulation with 1 μM (−)-isoproterenol. One clone giving the highest stimulation was subcloned by limiting dilution, and is referred to as CHO-Moβ3'.

EXAMPLE 5

Isolating and sequencing of the human β3AR gene.

Similar procedures set forth in the above examples to isolate and sequences the murine β3-adrenergic receptor gene were used in the isolation of the human β3-adrenergic receptor gene. A human genomic library was screened with the entire coding regions of the gene for the β1-adrenergic receptor of turkey Yarden et al., P.N.A.S., 83, 6795 (1986) and of the human gene for the β2-adrenergic receptor Emorine et al P.N.A.S. 84, 6995 (1987). The library was constructed in the BamHI sites of the EMBL4 vector from size-selected (15 to 20 kb) fragments of human placental DNA partially digested with Sau3a. For plague purification, probes of a 1.3 kb NcoI-AhaI restriction fragment of the human β2-adrenergic receptor and the 1.8 kb fragment of the turkey β1-adrenergic receptor were used Yarden et al., P.N.A.S., 83, 6795 (1986).

Among 43 positive clones two carried the gene coding for the human β1-adrenergic receptor and another two the gene for the β2-adrenergic receptor.

A family of 14 homologous clones consisting of a group of six identical clones, a second group of three identical clones and a third group of two identical clones and three independent clones displayed sequences homologous to both probes in a 2.1 kb BamHI and BglII fragment. From one clone, this 2.1 kb fragment was sequenced using the methods described by the chain termination method of Sanger et al., P.N.A.S., 74, 5463 (1977). This fragment that was entirely sequenced and shown to contain a gene coding for a polypeptide of 402 amino acids with a predicted size of 42,881 daltons.

EXAMPLE 6

Nucleotide sequence determination 2.5 kb SphI-BglII, and 2.2 kb XhoI-BglII fragments spanning the entire 3'-untranslated regions of the human and mouse β3-AR genomic genes, respectively, were inserted in both orientations into M13 and individual subclones were sequenced by the standard termination method (Taquence DNA sequencing kit, USB, Ohio). Primers were oliogonucleotides synthesized step by step during the course of sequence determination.

EXAMPLE 7

PCR-generated cDNA

Total RNA was prepared from frozen-powdered tissues and digested for 1 hr at 37° C. with 0.3 U of RNase-free DNase I (Promega, Wisconsin) per μg of nucleic acid in 100 mM Tris-HCl, pH 7.5; 50 mM $MgCl_2$, in the presence of 2 U/ml of placenta RNase inhibitor. 0.25 μg of RNA was then treated with 400 U of maloney murine leukemia virus reverse transcriptase (Gibco BRL) in 20 μl of PCR buffer containing 67 mM Tris-HCl, pH 8.4; 6.7 mM $MgCl_2$; 6.7 mM EDTA; 10 mM β-2-mercaptoethanol; 16 mM $(NH_4)_2SO_4$; and 0.1 mg/ml gelatine containing 0.4 mM each of dNTP, 10 mM random hexanucleotides and 2 U/ml RNase inhibitor. A control without reverse transcriptase was also run to ensure that amplification of the nucleotide sequence did not proceed from residual genomic DNA. 80 μl of PCR buffer containing 2.5 U of Thermophylus aquaticus polymerase (Perkin-Elmer-Cetus), 125 nM each of sense and antisense oligonucleotide primers, containing the following sequences, respectively:

5' GCTCCGTGGCCTCACGAGAA 3' (SEQ ID NO:7) and

5' CCCAACGGCCAGTGGCCAGTCAGCG 3' (SEQ ID NO:8), 125 mM each dNTP and 10% (v/v) dimethylsulfoxide was added to the cDNA samples which were submitted to 29 cycles at temperatures of 92° C., 1 minute; 57° C., 1.5 minutes; 72° C.; 1.5 minutes; followed by 7 minutes of extension at 72° C. in a temperature cycler (LEP-PREM).

EXAMPLE 8

Determination of mRNA transcription start sites

For nuclease S1 mapping single stranded DNA from a M13 subclone of the murine β3-AR gene promoter region (fragment BglII-NarI, was used as template for probe synthesis. After polymerization in the presence of α[$^{32}$P]-dATP, DNA was digested with Alw NI and the single stranded probe (380 nucleotides including 310 base from the β3-AR gene plus 70 bases from M13) was isolated on denaturing 6% polyacrylamide gels containing 7 M urea. Probe ($10^5$ c.p.m.) and total RNA (50 μg) were mixed in 30 μl of 40 mM Pipes buffer pH 6.4, containing 0.4 M NaCl, 1 mM EDTA and 70% formamide and denatured for 10 min at 85°. After hybridization (14–16 hr at 30° C.) Samples were digested for 30 min at 37° C. with 100–200 units of S1 nuclease in 400 μl of 50 mM sodium acetate, pH 4.8, 280 mM NaCl, 4.5 mM $ZnSO_4$. Following incubation for 10 min at 65° C., samples were phenol-extracted, concentrated by ethanol precipitation and analyzed on 6% acrylamide, 7 M urea sequencing gels.

For primer extension, oligonucleotide A74 (36-mer) having the following sequence (SEQ ID NO:9):

5' CTGGTCCAGGGGAGGGGACAGCAAG-GCATGAGAGCG 3' was labeled with T4-polynucleotide kinase hybridized ($5 \times 10^5$ c.p.m.) to 50 μg of total RNA, in 30 μl of 20 mN Tris-HCl, pH 8, 50 mM NaCl, 10 mM $MgCl_2$, 1 mm dithiotreitiol, and 0.1 mM EDTA, for 14–16 hr at 37° C. Nucleic acids were ethanol precipitated and incubated for 90 min at 42° C. after resuspension in 25 μl of 50 mM Tris-HCl, pH 8.3, 8 mM $MgCl_2$, 30 mM KCl containing 0.5 mM each DNTP, 50 units of placenta RNase inhibitor, and 40 units of avian myeloblastosis virus reverse transcriptase. Reactions were terminated by addition of 1 μl of both 0.5 M EDTA and pancreatic RNase A (1 mg/ml) and incubation for 30 min at 37° C. was performed. After phenol-extraction and ethanol precipitation in the presence of ammonium acetate (2 M final) samples were analyzed on 6% acrylamide, 7 M urea sequencing gels.

EXAMPLE 9

Expression of the entire human β3-adrenergic receptor

For expression in eukaryotic cells, a 3.7 kb SmaI-BglII restriction fragment from the human β3-adrenergic receptor gene was inserted under the control of the SV40 early promoter into a plasmid vector also containing the murine dihydrofolate reductase (DHFR) gene as a selectable marker as described by Larsky et al. Biotechnology, 2, pgs. 527–530 (1984). The resulting construct contained 4 bp of 5' untranslated region, the entire intron/exon sequence of the human β3-receptor gene with its own 3' untranslated region.

CHO cells or L cells (wherein the splicing of the gene can take place) deficient in DHFR, were grown in Ham's F12 medium (Seromed) supplemented with 10% fetal calf serum, 2 mM L-glutamine, 15 μg/ml glycine, 9.5 μg/ml hypoxanthine and 1.46 μg/ml thymidine. Transfection with 5 μg of the expression vector was performed by the calcium phosphate precipitation method as described by Tate et al. *EUR. J. Biochem.*, 196, pgs. 357–361 (1991). Stable transformants expressing the DHFR gene were screened for the expression of β adrenergic receptor by stimulation of cAMP accumulation with 1 μM (−)-isoproterenol.

EXAMPLE 10

Testing of various chemicals for β3-adrenergic receptor affinity

Preconfluent cells (5×10$^5$) were incubated at 37° C. for 20 minutes in 0.5 ml of Hank's buffer containing 20 mM HEPES (pH 7.4), 1 mM ascorbic acid, 1 mM isobutylmethylxanthine and various concentrations of agonists such as BRL 37344, (−)-isoproterenol and (−)-norepinephrine. After boiling for 5 minutes and centrifuging at 4,000 r.p.m. for 10 minutes at 4° C., the amount of cAMP produced was measured using the Amersham cAMP assay kit. Inhibition studies for cAMP accumulation were carried out by preincubating cells at 37° C. for 10 minutes with an antagonist such as propanolol, ICI 118551 and CGP 20712A before the addition of 5 nm (−)-isoproterenol. The mixture was incubated for an additional 20 minutes. Computer analysis of the data was carried out using the Graph-PAD program (copyright 1987 by M. J. Motulsky).

What is claimed is:

1. An isolated and purified polypeptide having β3-adrenergic receptor activity comprising the amino acid sequence of FIG. 4 (SEQ ID NO:6).

\* \* \* \* \*